(12) United States Patent
Wu et al.

(10) Patent No.: US 10,481,073 B2
(45) Date of Patent: *Nov. 19, 2019

(54) BASOPHIL ANALYSIS SYSTEM AND METHOD

(71) Applicant: Abbott Laboratories, Abbott Park, IL (US)

(72) Inventors: Jiong Wu, Los Gatos, CA (US); Michael R. Buhl, San Ramon, CA (US); Giacomo Vacca, San Jose, CA (US)

(73) Assignee: Abbott Laboratories, Abbott Park, IL (US)

( * ) Notice: Subject to any disclaimer, the term of this patent is extended or adjusted under 35 U.S.C. 154(b) by 79 days.

This patent is subject to a terminal disclaimer.

(21) Appl. No.: 15/801,055

(22) Filed: Nov. 1, 2017

(65) Prior Publication Data

US 2018/0136110 A1    May 17, 2018

Related U.S. Application Data

(63) Continuation of application No. 14/808,211, filed on Jul. 24, 2015, now Pat. No. 9,810,618, which is a continuation of application No. 13/456,744, filed on Apr. 26, 2012, now Pat. No. 9,091,625.

(60) Provisional application No. 61/482,549, filed on May 4, 2011.

(51) Int. Cl.
| | |
|---|---|
| *G01N 15/14* | (2006.01) |
| *G01N 21/64* | (2006.01) |
| *G01N 33/49* | (2006.01) |
| *G01N 15/10* | (2006.01) |
| *G01N 15/00* | (2006.01) |

(52) U.S. Cl.
CPC ..... *G01N 15/1434* (2013.01); *G01N 15/1459* (2013.01); *G01N 21/6428* (2013.01); *G01N 33/49* (2013.01); *G01N 2015/008* (2013.01); *G01N 2015/0069* (2013.01); *G01N 2015/1006* (2013.01); *G01N 2015/1402* (2013.01); *G01N 2015/1477* (2013.01); *G01N 2015/1486* (2013.01); *G01N 2015/1488* (2013.01); *G01N 2021/6439* (2013.01)

(58) Field of Classification Search
None
See application file for complete search history.

(56) References Cited

U.S. PATENT DOCUMENTS

| | | | |
|---|---|---|---|
| 4,661,913 A | 4/1987 | Wu et al. | |
| 4,727,020 A | 2/1988 | Recktenwald | |
| 4,882,284 A | 11/1989 | Kirchanski et al. | |
| 5,559,037 A | 9/1996 | Kim et al. | |
| 5,631,165 A | 5/1997 | Chupp et al. | |
| 5,656,499 A | 8/1997 | Chupp et al. | |
| 5,776,709 A | 7/1998 | Jackson et al. | |
| 5,812,419 A | 9/1998 | Chupp et al. | |
| 5,879,900 A | 3/1999 | Kim et al. | |
| 5,891,734 A | 4/1999 | Gill et al. | |
| 5,928,949 A | 7/1999 | Sakata et al. | |
| 5,939,326 A | 8/1999 | Chupp et al. | |
| 6,197,593 B1 | 3/2001 | Deka et al. | |
| 6,228,652 B1 | 5/2001 | Rodriguez et al. | |
| 6,551,831 B2 | 4/2003 | Gupta et al. | |
| 7,299,135 B2 | 11/2007 | Thayer | |
| 7,638,290 B2 | 12/2009 | Lefevre et al. | |
| 2004/0265830 A1 | 12/2004 | Szabo et al. | |
| 2006/0269970 A1 | 11/2006 | Paul et al. | |
| 2007/0111276 A1 | 5/2007 | Lefevre et al. | |
| 2007/0287145 A1 | 12/2007 | Mizukami et al. | |
| 2007/0298408 A1 | 12/2007 | Mizukami et al. | |
| 2009/0023129 A1 | 1/2009 | Xu et al. | |
| 2009/0061478 A1 | 3/2009 | Poulsen et al. | |
| 2010/0273168 A1 | 10/2010 | Krockenberger et al. | |

FOREIGN PATENT DOCUMENTS

| | | |
|---|---|---|
| JP | H0599919 | 4/1993 |
| JP | H06501106 | 1/1994 |
| JP | H09508703 | 9/1997 |
| JP | H09508705 | 9/1997 |
| JP | 2938976 | 6/1999 |
| JP | 2000501838 | 2/2000 |
| JP | 2001091513 | 4/2001 |
| JP | 2003510557 | 3/2003 |
| JP | 2003310299 | 11/2003 |
| JP | 2008500558 | 1/2008 |
| JP | 2010513929 | 4/2010 |

(Continued)

OTHER PUBLICATIONS

BD LSR II Flow Cytometer Brochure, BD Biosciences (2003).
Champert et al. (2004) "White-light supercontinuum generation in normally dispersive optical fiber using original multi-wavelength pumping system" Optics Express 12(19):4366-4371.
De Grooth et al. (1987) "Light-Scattering Polarization Measurements as a New Parameter in Flow Cytometry" Cytometry 8:539-544.
Flowguide, Flow cytometry guide, abcam® (2013).
Flowguide, Introduction to Flow Cytometry: A Learning Guide, Technical Manual, BD Biosciences (Apr. 2000).

(Continued)

*Primary Examiner* — Louise W Humphrey
*Assistant Examiner* — Srikanth Patury
(74) *Attorney, Agent, or Firm* — Edward J. Baba; Payal B. Sud; Bozicevic, Field & Francis LLP

(57) ABSTRACT

Provided herein are systems and methods for analyzing blood samples, and more specifically for performing a basophil analysis. In one embodiment, the systems and methods include: (a) staining a blood sample with an exclusive cell membrane permeable fluorescent dye; and then (b) using measurements of light scatter and fluorescence emission to distinguish basophils from other WBC sub-populations. In one embodiment, the systems and methods include performing a basophil cluster analysis of the blood sample, based on the combination of light scatter and fluorescence measurements.

21 Claims, 9 Drawing Sheets

(56) References Cited

FOREIGN PATENT DOCUMENTS

| JP | 2011069707 | 4/2011 |
| JP | 2013592594 | 1/2013 |
| WO | WO 2009/001868 | 12/2008 |
| WO | WO 2010/011583 | 1/2010 |
| WO | WO 2011/028437 | 3/2011 |

OTHER PUBLICATIONS

Fluorochromes, Table of Fluorochromes, SALK CCMI (2008).
LTAC Preservatives Handbook, 2013.
McCoy et al. (1991) "Sorting Minor Subpopulations of Cells: Use of Fluorescence as the Triggering Signal" *Cytometry* 12:268-274.
Sakata (2000) "Reagent Characteristics in the XE-2100 NRBC Channel" Sysmex Journal International, Technical Report, Series 9, 10(1):41-46.
Sysmex "Action mechanism of leukocytes by special reagents for automated leukocyte differentiation (DIFF channel)" The Cell Analysis Center—Scientific Bulletin Part 5, 2008, XP055183570.
Sysmex XE-2100 Operator's Manual, Chapter 7, Functional Description, Revised Jul. 2007, XP55182265.
SYTO-Dyes, Invitrogen Nucleic Staining Dyes, Webpage, 2009.
SYTO-Dyes, Molecular Probes Handbook, Table 8.3, 2009.

BASOPHIL ANALYSIS SYSTEM AND METHOD

CROSS REFERENCE TO RELATED APPLICATIONS

This application is a continuation of U.S. patent application Ser. No. 14/808,211 filed on Jul. 24, 2015, issued as U.S. Pat. No. 9,810,618, which is continuation of U.S. patent Ser. No. 13/456,744 filed on Apr. 26, 2012, issued as U.S. Pat. No. 9,091,625, which claims the benefit under 35 U.S.C. § 119(e) of U.S. Provisional Patent Application No. 61/482,549, titled, Method For Detecting and Analyzing Basophils, and filed on May 4, 2011, the entire disclosure of which is incorporated by reference herein.

This application is also related to U.S. patent application Ser. No. 13/456,729, filed on Apr. 26, 2012, titled "WHITE BLOOD CELL ANALYSIS SYSTEM AND METHOD," issued as U.S. Pat. No. 9,091,624; and U.S. patent application Ser. No. 13/456,738, filed on Apr. 26, 2012, titled "NUCLEATED RED BLOOD CELL ANALYSIS SYSTEM AND METHOD," issued as U.S. Pat. No. 9,103,759, the entire disclosures of which are herein incorporated by reference in their entirety.

BACKGROUND

This invention relates to hematology systems and methods. More specifically, this invention relates to systems and methods for analyzing blood samples to identify, classify, and/or quantify basophils in a sample of blood.

Basophils are a white blood cell (WBC) sub-population, which represent 1% or less of the total WBC count for a normal blood sample. Basophils are the least common sub-population of WBCs. Clinically, basophils are primarily involved in certain inflammatory and allergic reactions. Basophils discharge immune system mediators, such as histamine, serotonin, and heparin, to assist the flow of blood and to prevent blood clotting.

Traditionally, basophils are identified and counted manually by examination of microscope slides containing blood sample smears. The precision and accuracy of reviewing slides manually, however, is questionable because basophils are in such low concentrations relative to other WBC sub-populations. Furthermore, the need for well-trained medical technologists, and their associated cost of labor, makes manual review of slides even less commercially viable.

Alternative techniques for basophil detection include the use of antibodies in a flow cytometry analysis system. Numerous antibodies, such as, for example, CD203c, CD63 and FCεR1, were found to be sensitive and specific to basophil surface antigens. However, the cost of basophil antibody assays, the lengthy sample preparation and measurement process, and the requirement of a certified medical technologist having flow cytometry experience, make flow cytometry assay methods unpopular for most hospitals and laboratories.

Instead, basophils are most commonly reported as "best guess" estimates on automated, five-part differential hematology analyzers. In practice, the development of an accurate and efficient basophil assay has been a challenge because: (1) each blood sample is analyzed in less than a minute, including sample aspiration, sample-reagent interaction and incubation, as well as sample measurement, which is an insufficient time period for basophil identification; (2) basophil events number less than 1% in most blood samples; (3) basophils and lymphocytes share similar optical scattering characteristics, thus increasing the likelihood of misidentification; and (4) assays specifically designed for basophils would greatly increase the complexity and cost of the system.

BRIEF SUMMARY

Provided herein are systems and methods for analyzing blood samples, and more specifically for performing a basophil analysis. In one embodiment, the systems and methods include: (a) staining a blood sample with an exclusive cell membrane permeable fluorescent dye; and then (b) using measurements of light scatter and fluorescence emission to distinguish basophils from other WBC sub-populations. In one embodiment, the systems and methods include performing a basophil cluster analysis of the blood sample, based on the combination of light scatter and fluorescence measurements.

BRIEF DESCRIPTION OF THE FIGURES

The accompanying drawings, which are incorporated herein, form part of the specification. Together with this written description, the drawings further serve to explain the principles of, and to enable a person skilled in the relevant art(s), to make and use the systems and methods presented. In the drawings, like reference numbers indicate identical or functionally similar elements.

DETAILED DESCRIPTION

Figure 1:
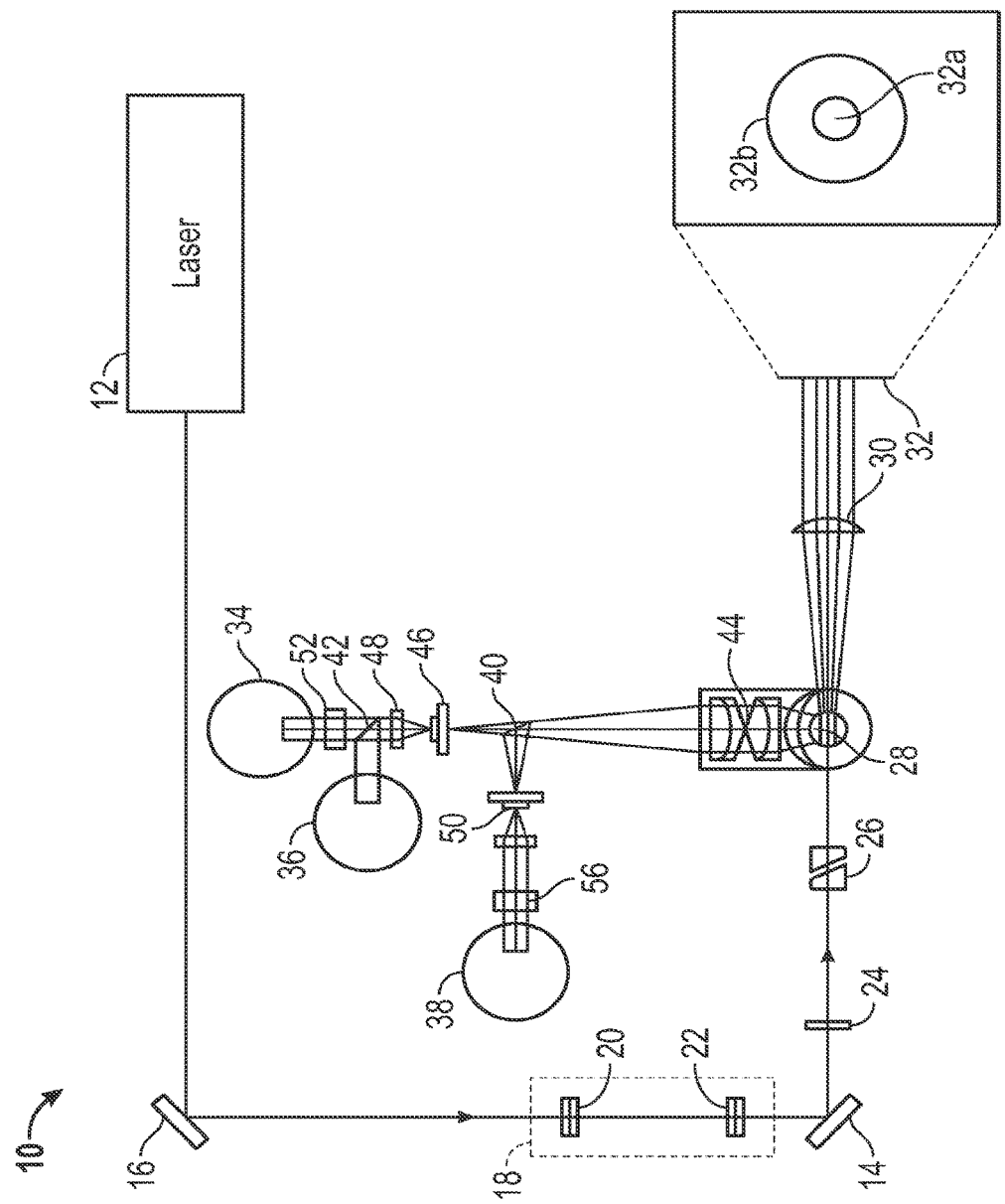
FIG. 1 is a schematic diagram illustrating a hematology instrument.

Provided herein are systems and methods for analyzing blood samples, and more specifically for performing a basophil analysis to identify, classify, and count basophils in a blood sample. In one embodiment, the systems and methods generally include: (a) staining a blood sample with an exclusive cell membrane permeable fluorescent dye; and then (b) using measurements of light scatter and fluorescence emission to distinguish basophils from other white blood cell (WBC) sub-populations. More specifically, example embodiments include a hematology analyzer having: an excitation source positioned to excite particles within the blood sample; a plurality of detectors positioned to measure light scatter and fluorescence emission; and a processor configured to (a) receive the measurements of light scatter and fluorescence emission and (b) perform a basophil cluster analysis of the blood sample, based on the received measurements. The basophil cluster analysis can include a "coarse" clustering of the received measurements, followed by a "fine" clustering of the received measurements. The fine clustering can utilize a multi-dimensional, probability distance metric as a determinant to combine similar clusters.

In one embodiment, the systems and methods include the screening of nuclei-containing events vs. non-nuclei-containing events by means of fluorescence staining and a fluorescence triggering strategy. As such, interference from unlysed red blood cells (RBCs), such as lysis-resistant red blood cells (rstRBCs), and RBC fragments is substantially eliminated prior to subsequent analysis. In other words, the systems and methods described herein utilize at least one fluorescent dye and a fluorescence triggering system to screen events containing nuclei, to thereby accurately and reliably identify and quantify WBC (and WBC sub-populations). A combination of light scattering information and fluorescence information is then used to further separate WBC sub-populations, and basophils specifically. The systems and methods disclosed thereby ensure accurate counting and differentiation of basophils.

(1) Use of a Plurality of Optical Channels and at Least One Fluorescence Channel for Analysis.

In one embodiment, the blood sample analysis is conducted by means of Multiple Angle Polarized Scattering Separation technology (MAPSS), with enhancement from fluorescence information. At least one photodiode, or at least one photomultiplier tube, or both at least one photodiode and at least one photomultiplier tube, are needed to detect light scattered by each blood cell passing through a flow cell. Two or more photodiodes are used for measuring axial light loss (ALL) signals, which measure about 0° scatter, and intermediate angle scatter (IAS) signals, which measure low angle (e.g., about 3° to about) 15° scatter. Two or more photomultiplier tubes are used for detecting 90° polarized side scatter (PSS) signals and 90° depolarized side scatter (DSS) signals. Additional photomultiplier tubes are needed for fluorescence (FL1) measurements within appropriate wavelength range(s), depending on the choice of wavelength of the source of light. Each event captured on the system thus exhibits a plurality of dimensions of information, such as ALL, IAS (one or more channels), PSS, DSS, and fluorescence (one or more channels). The information from these detection channels is used for further analysis of blood cells.

FIG. 1 is a schematic diagram illustrating the illumination and detection optics of an apparatus suitable for hematology analysis (including flow cytometry). Referring now to FIG. 1, an apparatus 10 comprises a source of light 12, a front mirror 14 and a rear mirror 16 for beam bending, a beam expander module 18 containing a first cylindrical lens 20 and a second cylindrical lens 22, a focusing lens 24, a fine beam adjuster 26, a flow cell 28, a forward scatter lens 30, a bulls-eye detector 32, a first photomultiplier tube 34, a second photomultiplier tube 36, and a third photomultiplier tube 38. The bulls-eye detector 32 has an inner detector 32a for 0° light scatter and an outer detector 32b for 7° light scatter.

In the discussion that follows, the source of light is preferably a laser. In alternative embodiments, a laser is selected that emits light at a wavelength between about 350 nm to about 700 nm; for example, in one embodiment a laser that emits light at about 488 nm is used. The source of light 12 can be a vertically polarized air-cooled Coherent Cube laser, commercially available from Coherent, Inc., Santa Clara, Calif. Lasers having wavelengths ranging from 350 nm to 700 nm can be used. Operating conditions for the laser are substantially similar to those of lasers currently used with "CELL-DYN" automated hematology analyzers. However, other sources of light can be used as well; such as, for example, lamps (e.g., mercury, xenon).

Additional details relating to the flow cell, the lenses, the focusing lens, the fine-beam adjust mechanism and the laser focusing lens can be found in U.S. Pat. No. 5,631,165, incorporated herein by reference, particularly at column 41, line 32 through column 43, line 11. The forward optical path system shown in FIG. 1 includes a spherical plano-convex lens 30 and a two-element photo-diode detector 32 located in the back focal plane of the lens. In this configuration, each point within the two-element photodiode detector 32 maps to a specific collection angle of light from cells moving through the flow cell 28. The detector 32 can be a bulls-eye detector capable of detecting axial light loss (ALL) and intermediate angle forward scatter (IAS). U.S. Pat. No. 5,631,165 describes various alternatives to this detector at column 43, lines 12-52.

The first photomultiplier tube 34 (PMT1) measures depolarized side scatter (DSS). The second photomultiplier tube 36 (PMT2) measures polarized side scatter (PSS), and the third photomultiplier tube 38 (PMT3) measures fluorescence emission from about 360 nm to about 750 nm, depending upon the fluorescent dye selected and the source of light employed. In one embodiment, PMT3 measures fluorescence emission from about 440 nm to about 680 nm, or more specifically from about 500 nm to about 550 nm. The photomultiplier tube collects fluorescent signals in a broad range of wavelengths in order to increase the strength of the signal. Side-scatter and fluorescent emissions are directed to these photomultiplier tubes by dichroic beam splitters 40 and 42, which transmit and reflect efficiently at the required wavelengths to enable efficient detection. U.S. Pat. No. 5,631,165 describes various additional details relating to the photomultiplier tubes at column 43, line 53 though column 44, line 4.

Sensitivity is enhanced at photomultiplier tubes 34, 36, and 38, when measuring fluorescence, by using an immersion collection system. The immersion collection system is one that optically couples the first lens 30 to the flow cell 28 by means of a refractive index matching layer, enabling collection of light over a wide angle. U.S. Pat. No. 5,631,165 describes various additional details of this optical system at column 44, lines 5-31.

The condenser 44 is an optical lens system with aberration correction sufficient for diffraction limited imaging used in high resolution microscopy. U.S. Pat. No. 5,631,165 describes various additional details of this optical system at column 44, lines 32-60.

The functions of other components shown in FIG. 1, i.e., a slit 46, a field lens 48, and a second slit 50, are described in U.S. Pat. No. 5,631,165, at column 44, line 63 through column 45, line 26. Optical filters 52 or 56 and a polarizer 52 or 56, which are inserted into the light paths of the photomultiplier tubes to change the wavelength or the polarization or both the wavelength and the polarization of the detected light, are also described in U.S. Pat. No. 5,631,165, at column 44, line 63 through column 45, line 26. Optical filters that are suitable for use herein include band-pass filters and long-pass filters.

The photomultiplier tubes 34, 36, and 38 detect either side-scatter (light scattered in a cone whose axis is approximately perpendicular to the incident laser beam) or fluorescence (light emitted from the cells at a different wavelength from that of the incident laser beam).

While select portions of U.S. Pat. No. 5,631,165 are referenced above, U.S. Pat. No. 5,631,165 is incorporated herein by reference in its entirety.

(2) Use of Fluorescent Dye(s).

WBCs contain a relatively high concentration of DNA in their nuclei. When appropriately designed, a fluorescent dye can be used to differentiate between different sub-populations of WBCs. For example, lymphocytes and basophils have different fluorescence signatures, despite having similar light scatter signatures. Further, mature RBCs do not contain DNA. Therefore, a fluorescent dye can be selected to differentiate between populations of blood cells. The purpose of the dye is to penetrate into live cells easily, bind DNA with high affinity, and emit strong fluorescence with adequate Stokes shift when the dye is excited by an appropriate source of light. The peak absorption of the dye in the visible band may substantially match the wavelength of the source of light (within 50 nm of the wavelength of the source of light, more preferably, within 25 nm of the wavelength of the source of light), in order to be properly excite the dye and achieve optimal results.

The fluorescent dye selected is preferably: 1) capable of binding nucleic acids, 2) capable of penetrating cell membranes of WBCs and nRBCs, 3) excitable at a selected wavelength when subjected to a source of light, 4) emits fluorescence upon excitation by the source of light, and 5) is biostable and soluble in a liquid. The dye may be selected from group consisting of: acridine orange, SYBR 11, SYBR Green series dye, hexidium iodide, SYTO 11, SYTO 12, SYTO 13, SYTO 14, SYTO 16, SYTO 21, SYTO RNA Select, SYTO 24, SYTO 25 and any equivalents thereof. The dye is used to "activate" WBCs and nRBCs, "screen out" unlysed RBCs and fragments of RBCs based on a fluorescence trigger configured in the hematology analyzer, and differentiate between sub-populations of WBCs. The dye is typically present at a concentration of from about 0.1 ng/mL to about 0.1 mg/mL. While various dyes are available, the dye selected is generally paired with the excitation source of the hematology analyzer such that a single exclusive dye is used to stain and excite fluorescence emission in nRBCs and all WBC sub-populations intended to be identified, quantified, and/or analyzed. As such, a single (i.e., exclusive) dye can be used to identify, quantify, and analyze basophils, amongst all other WBC subpopulations, at once.

In one embodiment, a fluorescent dye is provided in a reagent, with combinations of 1) at least one surfactant, 2) at least one buffer, 3) at least one salt, and/or 4) at least antimicrobial agent, in sufficient quantities for carrying out staining and activating up to $1,000 \times 10^3$ cells per microliter. The at least one surfactant, such as "TRITON" X-100 or saponin, is used to destroy the membranes of RBC, and reduce the sizes of fragments of RBCs. The at least one surfactant is typically present at a concentration of from about 0.001% to about 5%. The at least one antimicrobial agent, such as those from "TRIADINE" or "PROCLIN" families, is used to prevent the contamination of the reagent from microbes. The concentration of the at least one antimicrobial agent is sufficient to preserve the reagent for the shelf life required. The at least one buffer, such as phosphate buffered saline (PBS) or 4-(2-hydroxyethyl)-1-piperazineethanesulfonic acid (HEPES), is used to adjust the pH of reaction mixture for controlling lysis of RBCs and preserving WBCs. The at least one buffer is typically present at a concentration of from about 0.01% to about 3%. The pH typically ranges from about 3 to about 12. The at least one salt, such as NaCl or $Na_2SO_4$, is used to adjust the osmolality to increase the effect of lysing and/or optimize WBC preservation. The at least one salt may be present at a concentration of from about 0.01% to about 3%. In certain cases, the at least one buffer can serve as the at least one salt, or the at least one salt can serve as the at least one buffer.

In general, lower osmolality, or hypotonicity, is used to accelerate the lysis of RBCs. The osmolality typically ranges from about 20 to about 250 mOsm. Lysis of RBCs can be made to occur at a temperature above room temperature (e.g., between about 30° C. to about 50° C., such as about 40° C.) over a relatively short period of time (e.g., less than about 25 seconds, less than about 17 seconds, or even less than about 9 seconds), following mixing of the sample of blood and the reagent at a ratio of about one part by volume sample to about 35 parts by volume reagent.

The scatter and fluorescence data for analysis is generally collected with a plurality of optical channels and at least one fluorescence channel, as described above.

(3) Use of a Fluorescence Trigger.

Blood cells emit different magnitudes of fluorescence signals upon excitation of the fluorescent dye by a source of light. The differences in magnitude of fluorescence signals arise from the quantity of nucleic acids, namely DNA, inside the cells. The greater the quantity of DNA, the greater the likelihood of higher fluorescence signals. Also, efficacy of penetration of cell membranes, size of the dye, binding kinetics between the dye and DNA, affinity between the dye and DNA, and other factors, affect the fluorescence signals. Mature RBCs emit minimal fluorescence signals because there is no DNA within mature RBCs. Unlysed RBCs or RBC fragments do not emit fluorescence, although they may emit very weak auto-fluorescence. Basophils have also shown to have different fluorescence emission properties than lymphocytes.

As such, the systems and methods presented herein use a fluorescence trigger for collecting and analyzing WBCs and WBC sub-populations. In one embodiment, prior to basophil/lymphocyte differentiation, a fluorescence trigger is set between signals from RBCs and signals from WBCs (and nRBCs, when present). The optical and fluorescence information collected may then be used to distinguish (or differentiate) WBC sub-populations. For example, two-dimensional cytograms can be used to identify and distinguish particles.

As used herein, the expression "fluorescence information" means data collected from a fluorescence channel of a hematology analyzer. As used herein, the expression "fluorescence channel" means a detection device, such as a photomultiplier tube, set at an appropriate wavelength band for measuring the quantity of fluorescence emitted from a sample.

EXAMPLES

Figure 2A:
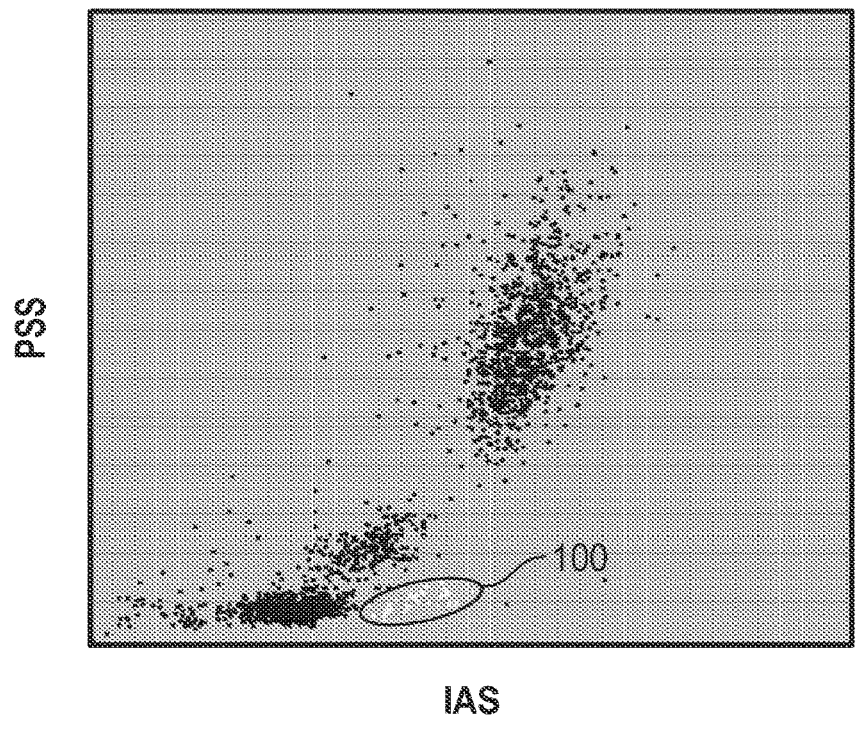
FIG. 2A is a cytogram of 90° polarized side scatter vs. intermediate angle scatter for a first sample of blood (SAMPLE 1).
Figure 2B:
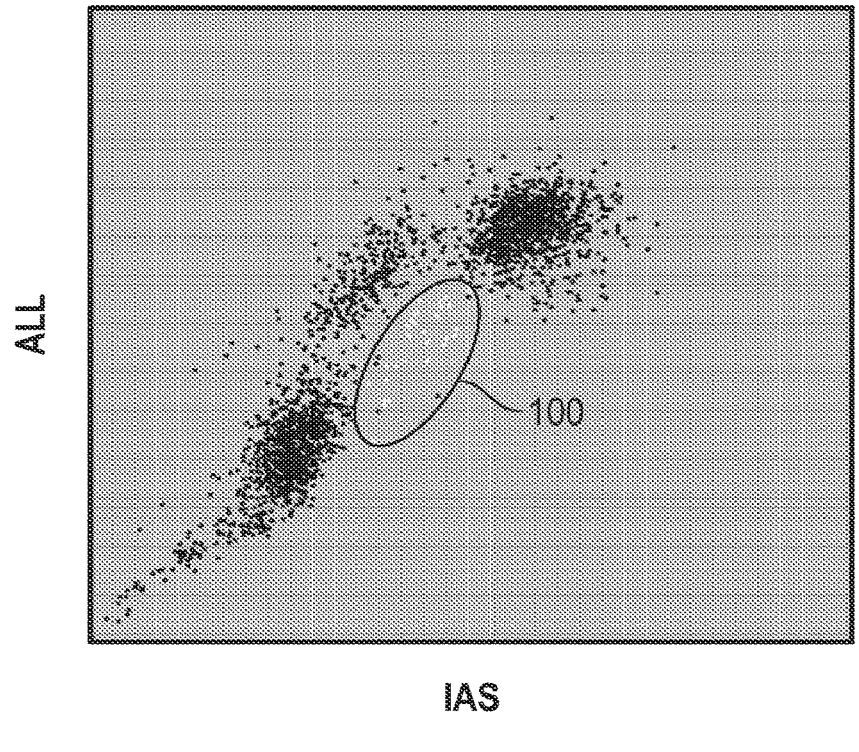
FIG. 2B is a cytogram of axial light loss vs. intermediate angle scatter for SAMPLE 1.
Figure 3A:
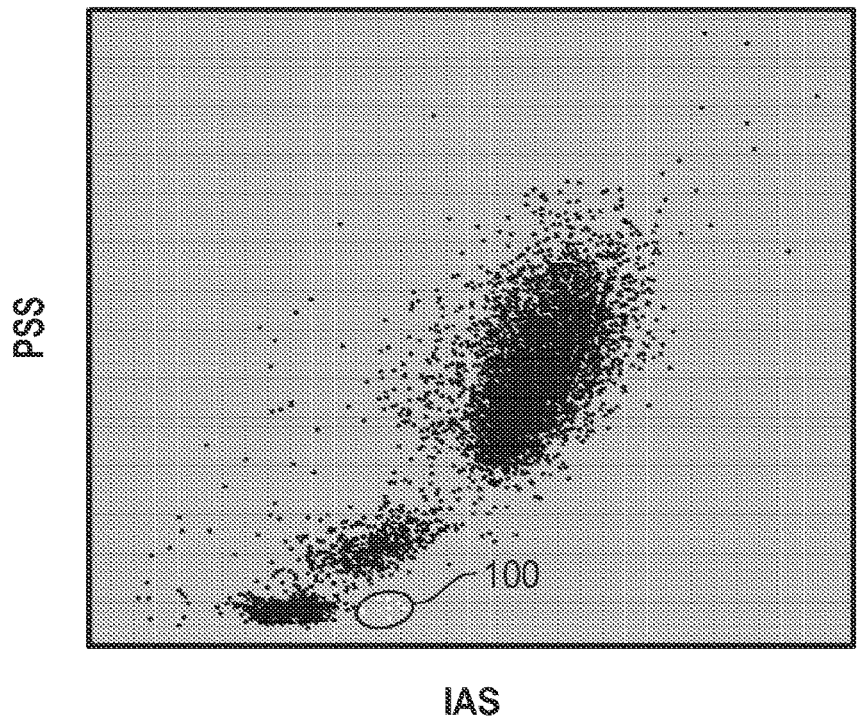
FIG. 3A is a cytogram of 90° polarized side scatter vs. intermediate angle scatter for a second sample of blood (SAMPLE 2).
Figure 3B:
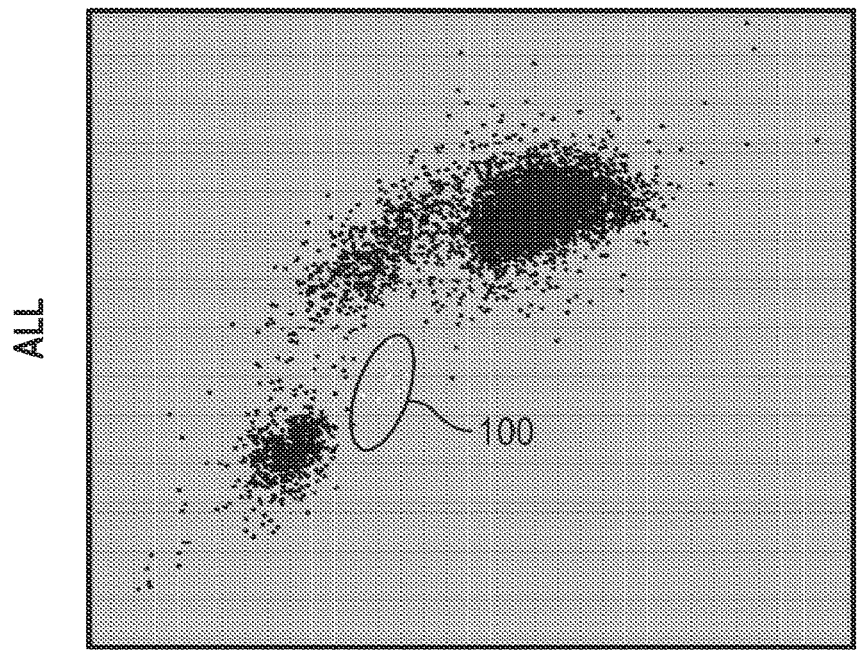
FIG. 3B is a cytogram of axial light loss vs. intermediate angle scatter for SAMPLE 2.

FIG. 2A is a cytogram of 90° polarized side scatter (PSS) vs. intermediate angle scatter (IAS) for a first sample of blood (SAMPLE 1) containing approximately 1.6% basophils. FIG. 2B is a cytogram of axial light loss (ALL) vs. IAS for SAMPLE 1. Basophils 100 were separated from the rest of the WBC sub-populations by manual gating. FIG. 3A is a cytogram of PSS vs. IAS for a second sample of blood (SAMPLE 2) containing approximately 0.2% basophils. FIG. 3B is a cytogram of ALL vs. IAS for SAMPLE 2. Basophils 100 were separated from the rest of the WBC sub-populations by manual gating. FIGS. 2A, 2B, 3A, and 3B illustrated that basophils can be separated by means of small angle side scatter (i.e., IAS, 3°-15°) and forward scatter (i.e., ALL, 0°-2°).

Figure 4:
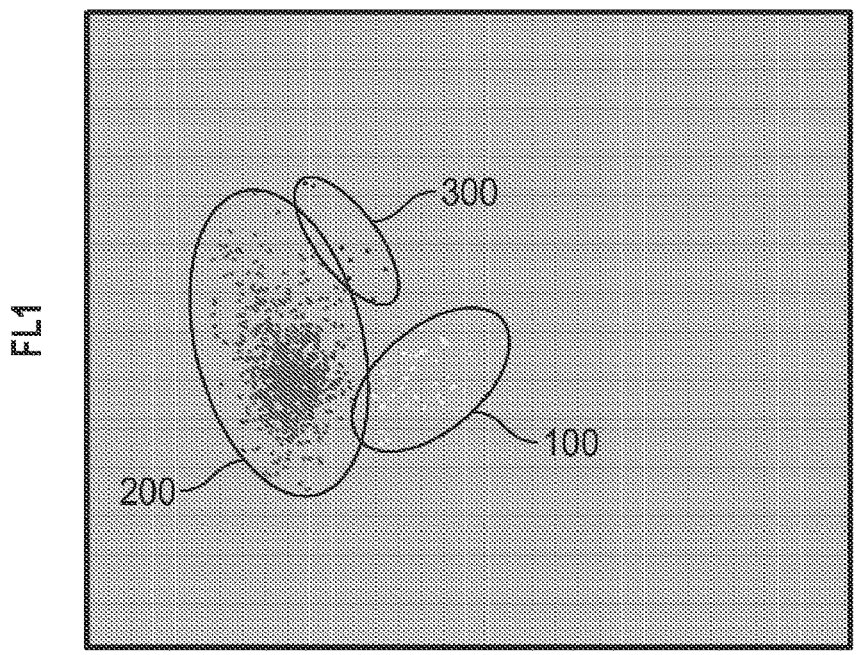
FIG. 4 is a cytogram of fluorescence vs. intermediate angle scatter for SAMPLE 1, showing lymphocytes and basophils.
Figure 5:
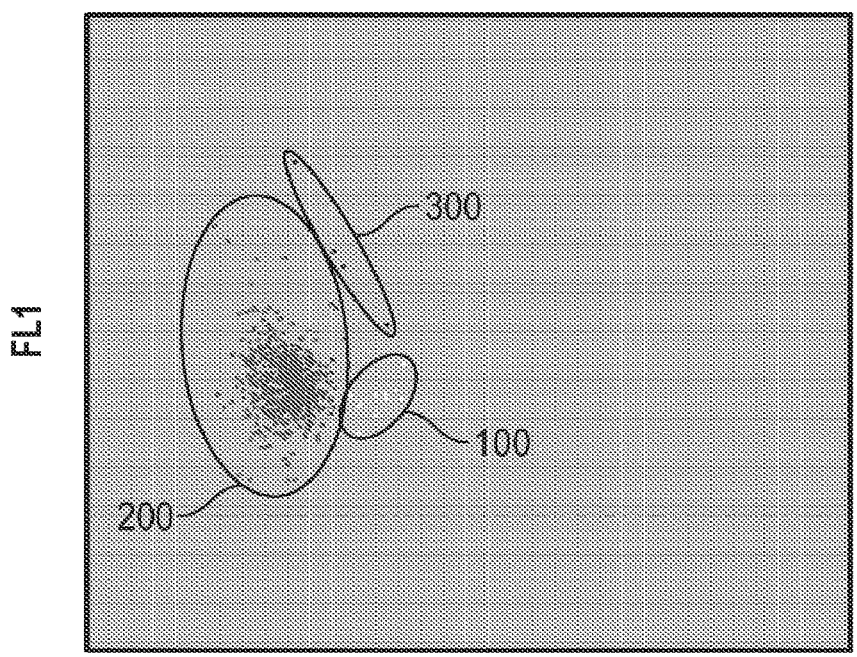
FIG. 5 is a cytogram of fluorescence vs. intermediate angle scatter for SAMPLE 2, showing lymphocytes and basophils.

FIG. 4 is a cytogram of fluorescence (FL1) vs. IAS for SAMPLE 1. Only lymphocytes 200, basophils 100, and residue monocytes 300 are shown in the cytogram. FIG. 5 is a cytogram of FL1 vs. IAS for SAMPLE 2. Only lymphocytes 200, basophils 100, and residue monocytes 300 are shown in the cytogram. FIGS. 4 and 5 illustrate that fluorescent dye staining enables further separation of basophils from WBC sub-populations (e.g., lymphocytes) in one or more fluorescence dimensions. Such separation is a result of the possible variations in potency of membranes, content of DNA, and staining efficiency among different WBC sub-populations. For example, treatment of WBCs with a WBC reagent containing acridine orange (3 μg/mL), at a temperature of 40° C., for a duration of 25 seconds, results in generally higher FL1 signals for lymphocytes, and lower FL1 signals for basophils. Thus, identification and quantification of basophils can be further facilitated with such a WBC reagent. In other words, basophils can be separated from lymphocytes by means of fluorescence emission signals when the WBC reagent causes basophils to emit fluorescence at different magnitudes from that emitted by lymphocytes (or other WBC sub-populations).

Figure 6A:
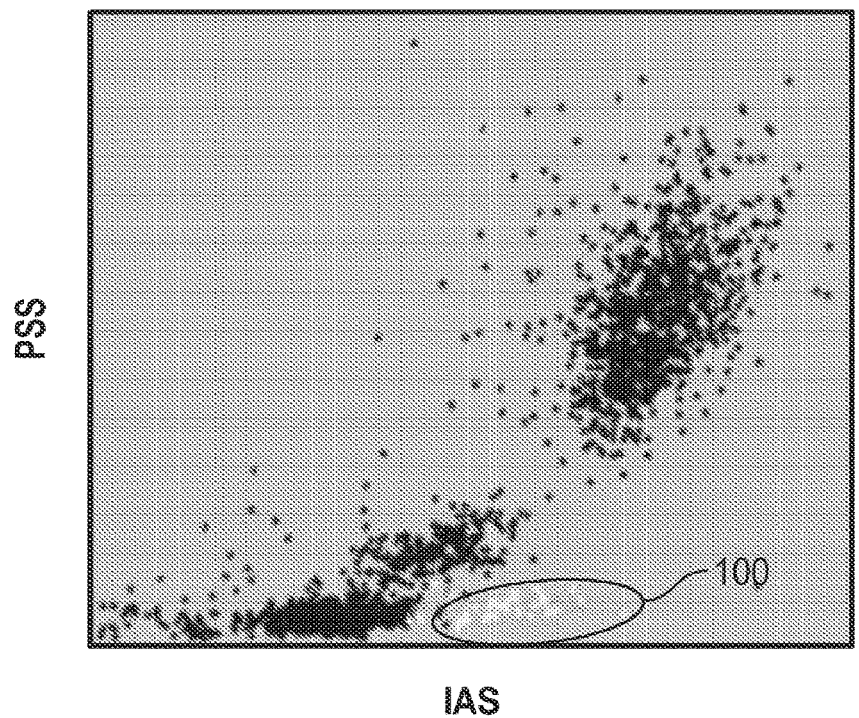
FIG. 6A is a cytogram of 90° polarized side scatter vs. intermediate angle scatter for SAMPLE 1.
Figure 6B:
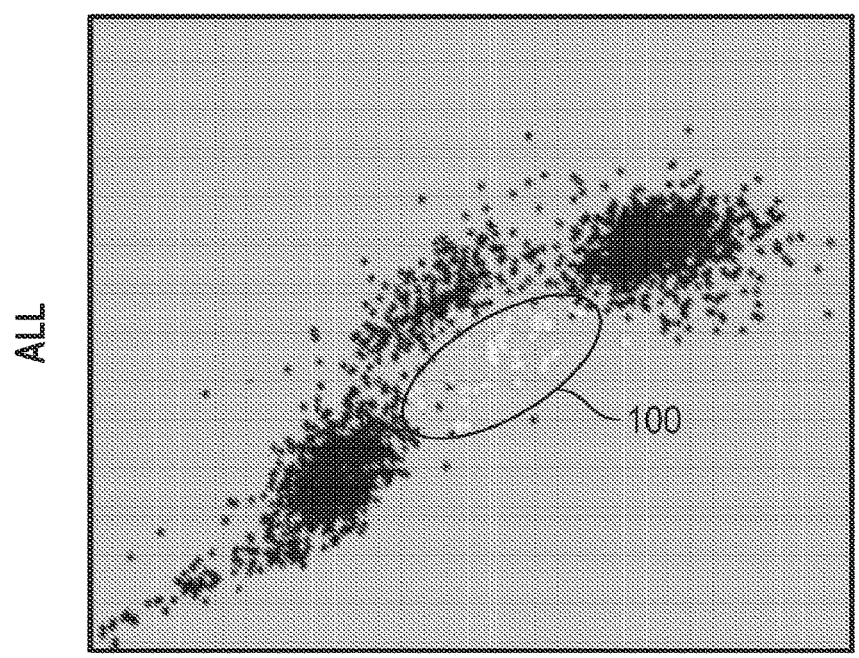
FIG. 6B is a cytogram of axial light loss vs. intermediate angle scatter for SAMPLE 1.
Figure 6C:
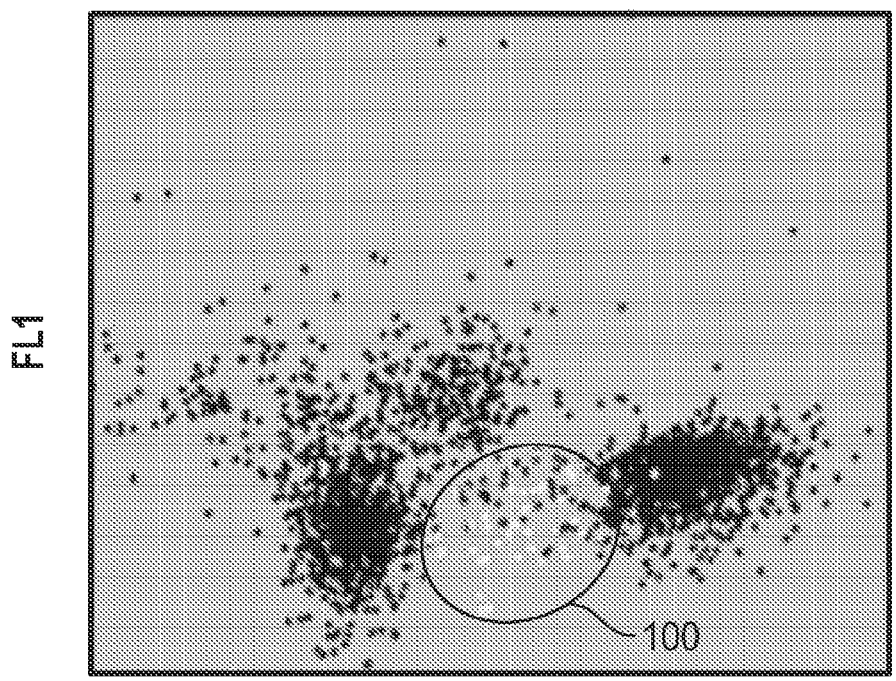
FIG. 6C is a cytogram of fluorescence vs. intermediate angle scatter for SAMPLE 1.
Figure 7A:
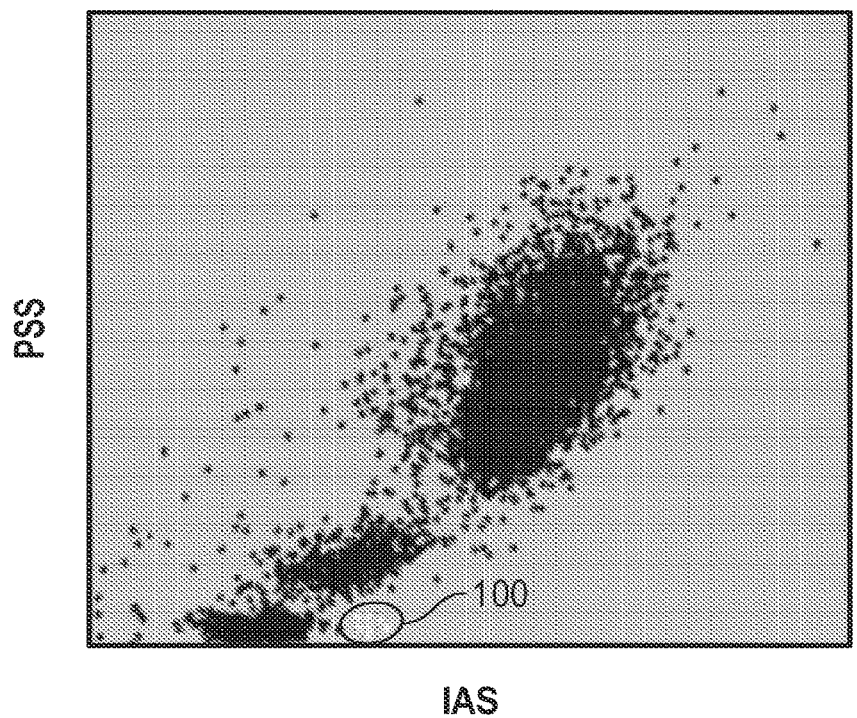
FIG. 7A is a cytogram of 90° polarized side scatter vs. intermediate angle scatter for a SAMPLE 2.
Figure 7B:
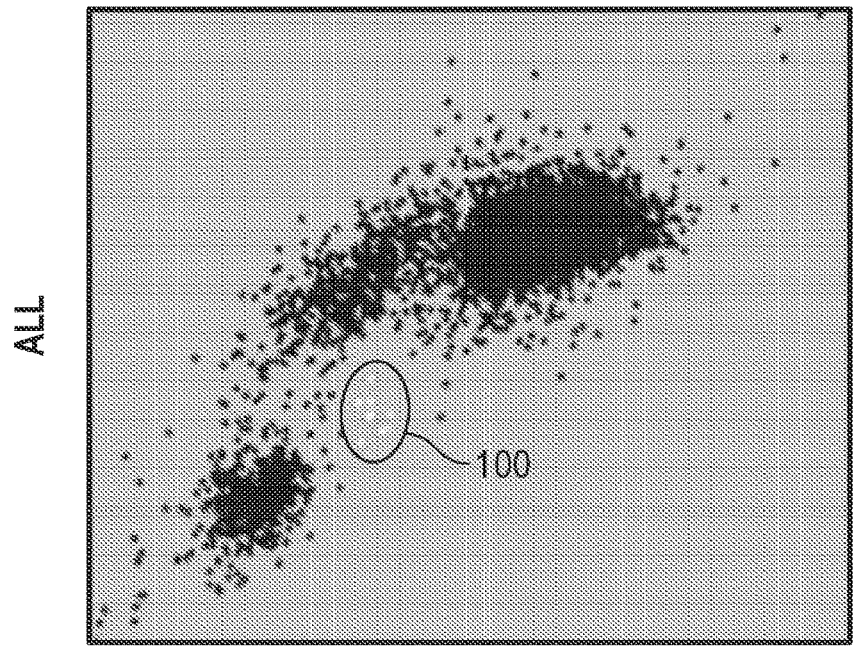
FIG. 7B is a cytogram of axial light loss vs. intermediate angle scatter for SAMPLE 2.
Figure 7C:
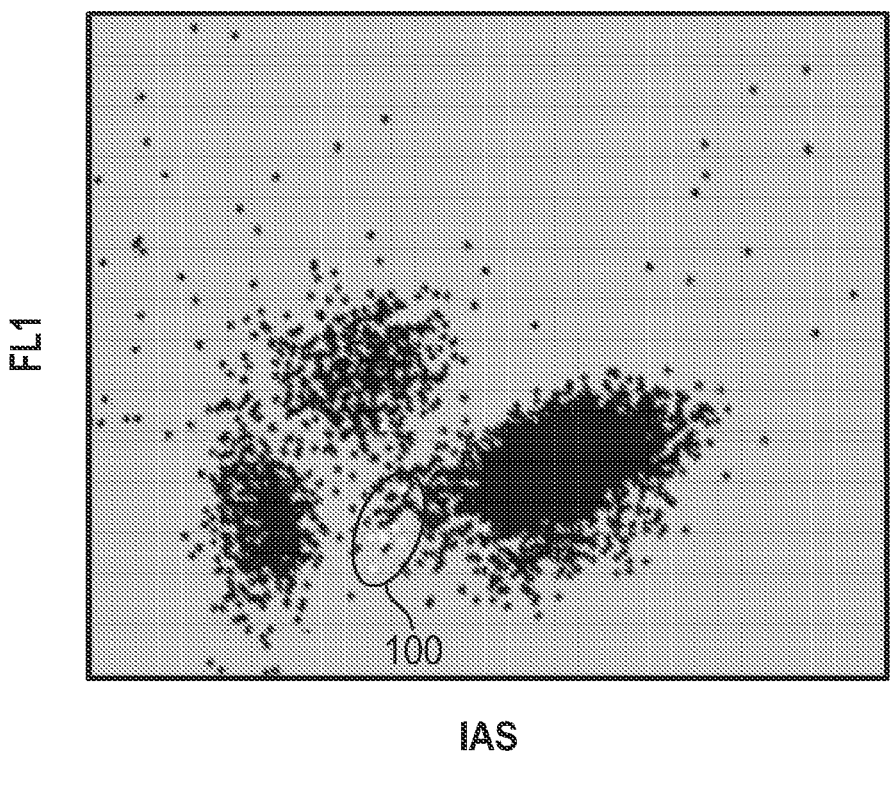
FIG. 7C is a cytogram of fluorescence vs. intermediate angle scatter for SAMPLE 2.

Further results are shown with reference to FIGS. 6A-6C and 7A-7C. For example, FIGS. 6A, 6B, 6C, show the separation of basophils using multiple dimensions (i.e., more than two dimensions (e.g., five dimensions)) for SAMPLE 1. More specifically, FIG. 6A is a cytogram of PSS vs. IAS for SAMPLE 1. FIG. 6B is a cytogram of ALL vs. IAS for SAMPLE 1. FIG. 6C is a cytogram of FL1 vs. IAS for SAMPLE 1. Basophils 100 were separated from the rest of the WBCs by a clustering analysis. FIGS. 7A, 7B, and 7C show the separation of basophils using multiple dimensions (i.e., more than two dimensions (e.g., five dimensions)) for SAMPLE 2. More specifically, FIG. 7A is a cytogram of PSS vs. IAS for SAMPLE 2. FIG. 7B is a cytogram of ALL vs. IAS for SAMPLE 2. FIG. 7C is a cytogram of FL1 vs. IAS for SAMPLE 2. Basophils 100 were separated from the rest of the WBCs by clustering analysis.

A comprehensive study of basophils was also conducted to evaluate the systems and methods described herein. A total of 56 samples of blood, with the percentage of basophils ranging from 0 to approximately 5%, were measured on a prototype analyzer operated according to the method described herein. The specimens were analyzed by both manual gating and a clustering analysis algorithm, in order to obtain the concentration of basophils, i.e., percentage of basophils (alternatively referred to herein as "% BA"). In operation, the clustering analysis algorithm applies an initial "coarse" clustering, which results in a large number of clusters. The algorithm then applies a second "fine" clustering step, utilizing a multi-dimensional, probability distance metric as a determinant to combine similar clusters. As a result, in this second step, the number of cells in a cluster is not used as a determinant, thereby preserving clusters having low concentrations of cells, such as basophils. All optical and fluorescence dimensions, including ALL, IAS, PSS, DSS and FL1, are utilized to determine the basophil cluster.

Figure 8:
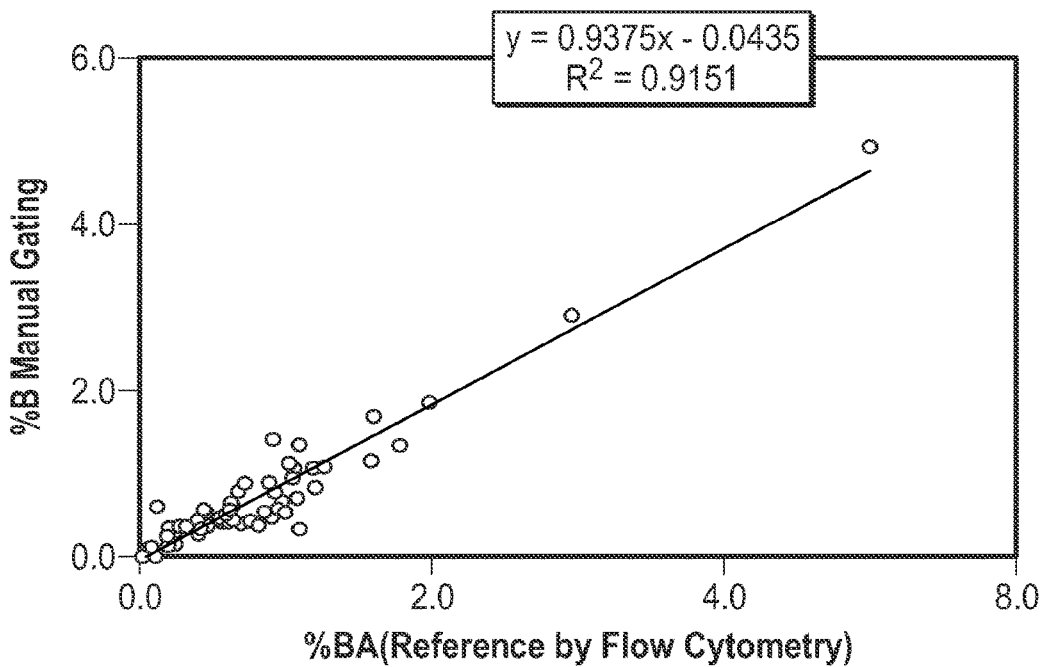
FIG. 8 is a plot showing correlation of basophil percentages analyzed by manual gating vs. basophil percentages determined by flow cytometry.
Figure 9:
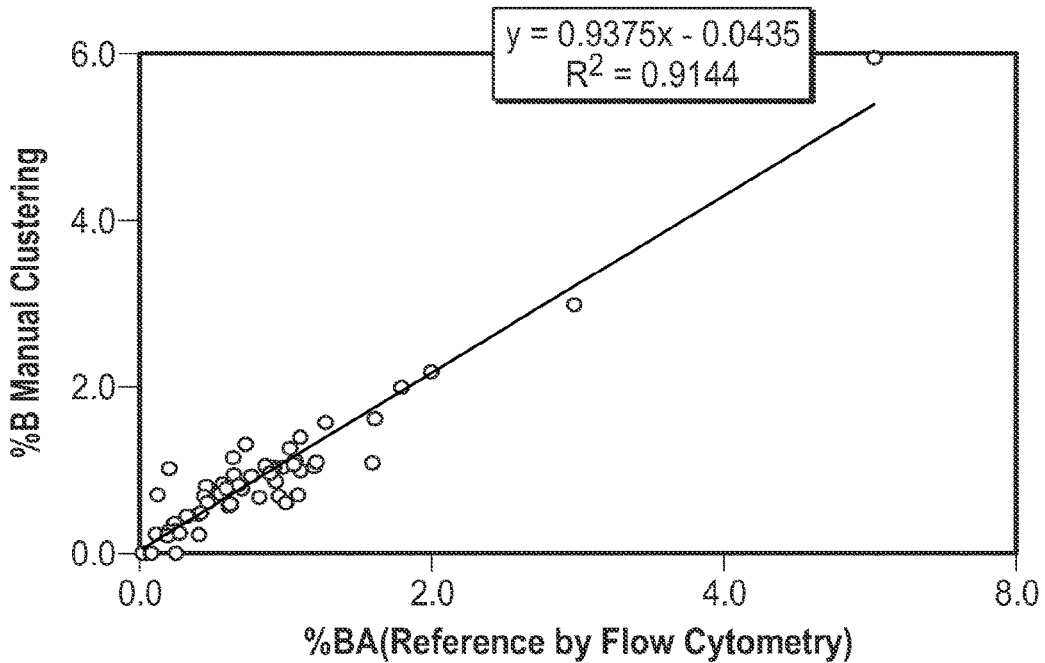
FIG. 9 is a plot showing correlation of basophil percentages analyzed by clustering vs. basophil percentages determined by flow cytometry.

Reference values were obtained by measuring the same set of samples with an Accuri® C6 flow cytometer, with a dual antibody basophils panel (CD45 and FCεR1). CD45 was measured in the FL3 channel and FCεR1 was measured in the FL4 channel. The results of this study are shown in FIGS. 8 and 9. More specifically, FIG. 8 is a plot showing correlation of basophil percentages analyzed by manual gating vs. basophil percentages determined by a reference flow cytometer. A total of 56 samples were measured and included in the correlation plot. FIG. 9 is a plot showing correlation of basophil percentages analyzed by clustering vs. basophil percentages determined by a reference flow cytometer. A total of 56 samples were measured and included in the correlation plot. Correlations were as follows:

$Y=0.9375X-0.0435$; $R^2=0.9151$ (see FIG. 8: manual gating vs. reference)

$Y=1.0721X+0.0348$; $R^2=0.9144$ (see FIG. 9: random clustering vs. reference)

As shown, excellent correlations were achieved between the method described herein and the reference method (i.e., using the Accuri® C6 flow cytometer). The separation between basophils and lymphocytes was quantitatively evaluated by Bhattacharyya distance as well. The mean Bhattacharyya distance between basophils and lymphocytes was 4.2±2.0 for the 56 samples, indicating overall reliable basophils analysis. There were only seven samples (12.5%) showing less optimal separation (Bhattacharyya distance <3.0, but all >2.5).

TABLE 1 compares results from the reference (i.e., using the Accuri® C6 flow cytometer), manual gating analysis, clustering analysis, and Bhattacharyya distance.

TABLE 1

|  | SAMPLE 1 | SAMPLE 2 |
| --- | --- | --- |
| % BA (Reference) | 1.60 | 0.19 |
| % BA (Manual gating) | 1.68 | 0.25 |
| % BA (Cluster analysis) | 1.62 | 0.22 |
| BA-LY (Bhattacharyya distance) | 4.26 | 5.27 |

Satisfactory separation of basophils from lymphocytes was achieved by optimizing the WBC reagent to generate different optical scatter signals for basophils and lymphocytes, and utilizing a fluorescent dye to stain WBCs to emit different levels of fluorescence signals. Accurate quantification of basophils can be achieved by the method described herein. In addition, the method described herein is fast, simple, and cost effective. Basophils can be identified and quantified in under a minute, typically under 30 seconds, with as few as one WBC reagent. The formulation of the WBC reagent enables basophils to be observed as a separate population in a plurality of optical dimensions and in at least one fluorescence dimension. Further, identification and quantification of basophils can be carried out simultaneously with the identification and quantification of all WBC sub-populations, in a single assay.

ADDITIONAL EMBODIMENTS

In one embodiment, the systems and methods include: (a) optimizing a WBC reagent by appropriate selection of surfactant(s), concentration(s) of surfactant(s), appropriate selection of WBC stabilizing agent(s), concentration(s) of WBC stabilizing agent(s), final pH of the reaction mixture, and osmolality; (b) including a dye for staining nuclei in the WBC reagent to stain WBCs; and (c) analyzing basophils that appear after processing raw data files using an automatic clustering algorithm. Raw data files may include events having at least five dimensions of information; namely ALL, IAS, PSS, DSS and FL1, along with time tags and other relevant information. The optimizing component enables the differentiation of basophils from lymphocytes in at least one of the optical dimensions.

In another embodiment, there is provided a hematology analyzer for conducting a basophil analysis on a blood sample that has been dyed with a fluorescent dye, wherein the fluorescent dye is cell membrane permeable and nucleic acid binding. The analyzer comprises an excitation source positioned to excite particles within the blood sample.

In another embodiment, there is provided a method for detecting basophils by means of an automated hematology analyzer. The method includes the steps of: (a) diluting a sample of whole blood with at least one white blood cell reagent; (b) incubating the diluted sample of step (a) for a sufficient period of time within a selected temperature range to lyse red blood cells, preserve white blood cells, and allow at least one fluorescent dye to stain white blood cells; (c) delivering the incubated mixture of step (b) to a flow cell in a stream; (d) exciting the sample by means of a source of light as the sample passes through the flow cell; (e) collecting a plurality of optical scatter signals and at least one fluorescence emission signal simultaneously; and (f) identifying and quantifying basophils by means of the optical scatter signals and fluorescence emission signals collected in step (e). The at least one white blood cell reagent may comprise: (a) at least one surfactant, (b) at least one buffer or at least one salt or at least one buffer and at least one salt, (c) at least one antimicrobial agent, and (d) at least one fluorescent dye, wherein the formulation of the at least one white blood cell reagent enables basophils to be observed as a separate population in a plurality of optical dimensions and in at least one fluorescence dimension. Basophils may be detected and analyzed during a white blood cell differential analysis, without using a reagent designated solely for detecting and analyzing basophils. The basophils may be separated from lymphocytes by means of small angle side scatter and forward scatter. The basophils may be separated from lymphocytes by means of fluorescence emission signals when basophils emit fluorescence at a different magnitude from that emitted by lymphocytes. The basophils may be analyzed by means of both optical information and fluorescence information. The basophils may differentiated by means of random clustering through the use of a plurality of dimensions of optical information and at least one dimension of fluorescence information. The light source may have a wavelength of from about 350 nm to about 700 nm. The fluorescence emission may be collected at from about 360 nm to about 700 nm, by means of band-pass filters or long-pass filters. Identification and quantification of basophils, and identification and quantification of the remainder of white blood cells, may be carried out simultaneously in a single assay.

In another embodiment, there is provided a method for detecting basophils by means of an automated hematology analyzer, the method comprising the steps of: (a) diluting a sample of whole blood with at least one white blood cell reagent; (b) incubating the diluted sample of step (a) for a sufficient period of time within a selected temperature range to lyse red blood cells, preserve white blood cells, and allow at least one fluorescent dye to stain white blood cells; (c) delivering the incubated mixture of step (b) to a flow cell in a stream; (d) exciting the sample by means of a source of light as the sample passes through the flow cell; (e) collecting a plurality of optical scatter signals and at least one fluorescence emission signal simultaneously; and (f) identifying and quantifying basophils by means of the optical scatter signals and fluorescence emission signals collected in step (e).

A feature of the systems and methods described herein includes separating basophils from neutrophils, monocytes and eosinophils by means of Multiple Angle Polarized Scatter Separation technology. Basophils and the other three white blood cell sub-populations show substantially different signals for the axial light loss channel (ALL), which measures 0° scatter, the intermediate angle scatter channel (IAS), which measures 3°-15° scatter, the 90° polarized side scatter channel (PSS), and the 90° depolarized side scatter channel (DSS). Another feature of the method involves separating basophils from lymphocytes by optical scattering information (such as, IAS information, ALL information, and PSS information) and fluorescence information.

In another embodiment, there is provided a hematology analyzer for conducting a basophil analysis on a blood sample that has been dyed with a fluorescent dye, wherein the fluorescent dye is cell membrane permeable and nucleic acid binding. The analyzer includes an excitation source positioned to excite particles within the blood sample. The excitation source can be a laser. The analyzer further includes a plurality of detectors including: (1) an axial light loss detector positioned to measure axial light loss from the excited blood sample, (2) an intermediate angle scatter detector positioned to measure intermediate angle scatter from the excited blood sample, (3) a side scatter detector positioned to measure 90° side scatter from the excited blood sample, and (4) a fluorescence detector positioned to measure fluorescence emitted from the excited blood sample. The axial light loss detector can measure axial light loss at 0° scatter. The intermediate angle scatter detector can measure light angle scatter at about 3° to about 15°. The plurality of detectors can include one or more photomultiplier tubes. The analyzer further includes a processor configured to: (a) receive the measurements of (1) axial light loss, (2) intermediate angle scatter, (3) 90° side scatter, and (4) fluorescence from the plurality of detectors, and (b) perform a basophil cluster analysis of the blood sample, based on all four measurements. The basophil cluster analysis may include a coarse clustering of the received measurements. The basophil cluster analysis may further include a fine clustering of the received measurements, utilizing a multi-dimensional, probability distance metric as a determinant to combine similar clusters.

The side scatter detector may be a polarized side scatter detector positioned to measure 90° polarized side scatter from the excited blood sample. The processor thus may be further configured to distinguish basophils within the blood sample from lymphocytes within the blood sample, based on the measurements of (1) axial light loss, (2) intermediate angle scatter, (3) 90° polarized side scatter, and (4) fluorescence. The analyzer may also include a depolarized side scatter detector positioned to measure 90° depolarized side scatter from the excited blood sample. The processor may further be configured to distinguish basophils within the blood sample from neutrophils, monocytes, and eosinophils within the blood sample, based on the measurements of (1) axial light loss, (2) intermediate angle scatter, and (3) 90° side scatter. The processor may be further configured to pre-screen the received measurements to remove from consideration any particles that do not meet the fluorescence threshold.

The hematology analyzer may further comprise an incubation subsystem for diluting the blood sample with a reagent. The reagent can include the fluorescent dye and a lysing agent. The reagent may include: (a) at least one surfactant, (b) at least one buffer or at least one salt, (c) at least one antimicrobial agent, and (d) the fluorescent dye. The incubation subsystem may be configured to incubate the blood sample with the reagent for a period of time of less than about 30 seconds. The incubation subsystem may be configured to incubate the blood sample with the reagent at a temperature ranging from about 30° C. to about 50° C. The incubation subsystem may be configured to incubate the blood sample with the reagent at a temperature of about 40° C.

In another embodiment, there is provided a method of performing a basophil analysis with an automated hematology analyzer. The method comprises: (a) diluting a sample of whole blood with a reagent, wherein the reagent includes a red blood cells (RBC) lysing agent and a cell membrane permeable, nucleic acid binding fluorescent dye; (b) incubating the diluted blood sample of step (a) for an incubation period of less than about 30 seconds, at a temperature ranging from about 30° C. to about 50° C.; (c) delivering the incubated sample from step (b) to a flow cell in the hematology analyzer; (d) exciting the incubated sample from step (c) with an excitation source as the incubated sample traverses the flow cell; (e) collecting a plurality of light scatter signals and a fluorescence emission signal from the excited sample; and (f) performing a basophil cluster analysis based on all the signals collected in step (e). The basophil cluster analysis may include a coarse clustering of the collected signals. The basophil cluster analysis may further include a fine clustering of the collected signals, utilizing a multi-dimensional, probability distance metric as a determinant to combine similar clusters. The reagent may include: (a) at least one surfactant, (b) at least one buffer or at least one salt, (c) at least one antimicrobial agent, and (d) at least one fluorescent dye. The excitation source may have a wavelength of from about 350 nm to about 700 nm. The excitation source may have a wavelength of about 488 nm. The plurality of light scatter signals may include: (1) axial light loss, (2) intermediate angle scatter, and (3) 90° side scatter. The plurality of light scatter signals may otherwise include: (1) axial light loss, (2) intermediate angle scatter, (3) 90° polarized side scatter, and (4) 90° depolarized side scatter.

In one embodiment, the invention is directed towards one or more computer systems capable of carrying out the functionality described herein. For example, any of the method/analysis steps discussed herein may be implemented in a computer system having one or more processors, a data communication infrastructure (e.g., a communications bus, cross-over bar, or network), a display interface, and/or a storage or memory unit. The storage or memory unit may include computer-readable storage medium with instructions (e.g., control logic or software) that, when executed, cause the processor(s) to perform one or more of the functions described herein. The terms "computer-readable storage medium," "computer program medium," and "computer usable medium" are used to generally refer to media such as a removable storage drive, removable storage units, data transmitted via a communications interface, and/or a hard disk installed in a hard disk drive. Such computer program products provide computer software, instructions, and/or data to a computer system, which also serve to transform the computer system from a general purpose computer into a special purpose computer programmed to perform the particular functions described herein. Where appropriate, the processor, associated components, and equivalent systems and sub-systems thus serve as examples of "means for" performing select operations and functions. Such "means for" performing select operations and functions also serve to transform a general purpose computer into a special purpose computer programmed to perform said select operations and functions.

The systems and methods thus provide a fast, simple, low cost method of detecting and analyzing basophils on automated hematology analyzers. The assay can be performed within a minute, including no more than 30 seconds for sample incubation and no more than 10 seconds for sample measurement. One white blood cell reagent can be used to lyse red blood cells and differentiate white blood cells, including the least common sub-population of white blood cells, namely basophils.

CONCLUSION

The foregoing description of the invention has been presented for purposes of illustration and description. It is not intended to be exhaustive or to limit the invention to the precise form disclosed. Other modifications and variations may be possible in light of the above teachings. The embodiments were chosen and described in order to best explain the principles of the invention and its practical application, and to thereby enable others skilled in the art to best utilize the invention in various embodiments and various modifications as are suited to the particular use contemplated. It is intended that the appended claims be construed to include other alternative embodiments of the invention; including equivalent structures, components, methods, and means.

The above Detailed Description refers to the accompanying drawings that illustrate one or more exemplary embodiments. Other embodiments are possible. Modifications may be made to the embodiment described without departing from the spirit and scope of the present invention. Therefore, the Detailed Description is not meant to be limiting. Further, the Summary and Abstract sections may set forth one or more, but not all exemplary embodiments of the present invention as contemplated by the inventor(s), and thus, are not intended to limit the present invention and the appended claims in any way.

What is claimed is:

1. A hematology analyzer for conducting a basophil analysis on a blood sample that contains a plurality of basophils and lymphocytes, the analyzer comprising:
   an excitation source positioned to excite particles within the blood sample;
   a detector unit comprising a fluorescence detector positioned to measure fluorescence emitted from the excited blood sample; and
   a processor;
   a non-transitory computer-readable memory medium comprising instructions that cause the processor to:
      excite the blood sample with an excitation source in a flow cell;
      collect a plurality of fluorescence emission signals from the excited sample;
      prior to performing a basophil analysis, exclude nuclei-free events and retain nuclei-containing events using only a fluorescence trigger that is limited to fluorescence emission signals and is set to a fluorescence magnitude that is greater than fluorescence emission signals from RBCs, including RBC fragments, and is less than fluorescence emission signals from white blood cells (WBCs); and perform a basophil cluster analysis on the nuclei-containing events.

2. The hematology analyzer of claim 1, wherein the basophil cluster analysis includes a coarse clustering of the received measurements.

3. The hematology analyzer of claim 2, wherein the basophil cluster analysis further includes a fine clustering of the nuclei-containing events, utilizing a multi-dimensional, probability distance metric as a determinant to combine similar clusters.

4. The hematology analyzer of claim 1, wherein the detector unit comprises a side scatter detector that is a polarized side scatter detector positioned to measure 90° polarized side scatter from the excited blood sample.

5. The hematology analyzer of claim 4, wherein the detector unit further comprises an axial light loss detector and an intermediate angle scatter detector and wherein the processor is further configured to distinguish basophils within the blood sample from lymphocytes within the blood sample, based on the measurements of (1) axial light loss by the axial light loss detector, (2) intermediate angle scatter by the intermediate angle scatter detector, (3) 90° polarized side scatter by the polarized side scatter detector, and (4) fluorescence by the fluorescence detector.

6. The hematology analyzer of claim 4, further comprising:

a depolarized side scatter detector positioned to measure 90° depolarized side scatter from the excited blood sample.

7. The hematology analyzer of claim 1, wherein the detector unit further comprises an axial light loss detector, an intermediate angle scatter detector, a side scatter detector and wherein the processor is further configured to distinguish basophils within the blood sample from neutrophils, monocytes, and eosinophils within the blood sample, based on the measurements of (1) axial light loss by the intermediate angle scatter detector, (2) intermediate angle scatter by the intermediate angle scatter detector, and (3) 90° side scatter by the side scatter detector.

8. The hematology analyzer of claim 1, wherein the detector unit further comprises an axial light loss detector, an intermediate angle scatter detector, a 90° polarized side scatter detector and wherein the processor is further configured to distinguish basophils within the blood sample from neutrophils, monocytes, and eosinophils within the blood sample, based on the measurements of (1) axial light loss, (2) intermediate angle scatter, (3) 90° polarized side scatter, and (4) fluorescence.

9. The hematology analyzer of claim 1, wherein the detector unit further comprises a axial light loss detector that measures axial light loss at 0° scatter.

10. The hematology analyzer of claim 1, wherein the detector unit further comprises a intermediate angle scatter detector that measures light angle scatter at about 3° to about 15°.

11. The hematology analyzer of claim 1, wherein the detector unit comprises one or more photomultiplier tubes.

12. The hematology analyzer of claim 1, wherein the excitation source is a laser.

13. The hematology analyzer of claim 1, further comprising:

an incubation subsystem for diluting the blood sample with a reagent.

14. The hematology analyzer of claim 13, wherein the reagent includes (a) at least one surfactant, (b) at least one buffer or at least one salt, (c) at least one antimicrobial agent, and (d) a fluorescent dye.

15. The hematology analyzer of claim 13, wherein the incubation subsystem is configured to incubate the blood sample with the reagent for a period of time of less than 30 seconds.

16. The hematology analyzer of claim 13, wherein the incubation subsystem is configured to incubate the blood sample with the reagent at a temperature ranging from 30° C. to 50° C.

17. The hematology analyzer of claim 13, wherein the incubation subsystem is configured to incubate the blood sample with the reagent at a temperature of 40° C.

18. The hematology analyzer of claim 1, wherein the processor is configured to perform a multi-dimensional basophil cluster analysis on the nuclei-containing events.

19. The hematology analyzer of claim 1, wherein the non-transitory computer-readable memory medium further comprises instructions to dilute the blood sample with a reagent that includes a red blood cell (RBC) lysing agent and a cell membrane permeable, nucleic acid binding fluorescent dye.

20. The hematology analyzer of claim 19, wherein the non-transitory computer-readable memory medium further comprises instructions to incubate the diluted blood sample for an incubation period of time.

21. The hematology analyzer of claim 20, wherein the non-transitory computer-readable memory medium further comprises instructions to deliver the incubated sample to a flow cell in the hematology analyzer.

* * * * *